United States Patent
Corey et al.

(10) Patent No.: US 6,316,264 B1
(45) Date of Patent: Nov. 13, 2001

(54) TEST STRIP FOR THE ASSAY OF AN ANALYTE IN A LIQUID SAMPLE

(75) Inventors: Paul F. Corey, Elkhart; Michael J. Pugia, Granger; Gary E. Rehm, Elkhart, all of IN (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 09/466,637

(22) Filed: Dec. 17, 1999

(51) Int. Cl.[7] ................................................. G01N 31/22
(52) U.S. Cl. ......................... 436/66; 422/56; 422/57; 436/110; 436/164; 436/169
(58) Field of Search ........................... 436/519, 110, 436/66, 164, 169; 252/408.1; 422/58, 64, 56, 57; 435/4

(56) References Cited

U.S. PATENT DOCUMENTS

| 5,360,628 | 11/1994 | Butland | 427/7 |
|---|---|---|---|
| 5,435,505 | 7/1995 | Martin | 246/187 |
| 5,445,930 | 8/1995 | Harada et al. | 430/588 |
| 5,453,505 | 9/1995 | Lee et al. | 544/124 |
| 5,885,677 | * 3/1999 | Gosselin | 428/40.1 |

FOREIGN PATENT DOCUMENTS

WO 97/32884  9/1997  (WO) ................ C07D/487/22

* cited by examiner

*Primary Examiner*—Jill Warden
*Assistant Examiner*—Samuel P. Siefke
(74) *Attorney, Agent, or Firm*—Jerome L. Jeffers (57) ABSTRACT

An improved test strip for determining the presence or concentration of unknown or a constituent in a liquid test sample is disclosed. The test strip comprises a support strip and a test pad, wherein the test pad includes a carrier matrix incorporating a reagent composition capable of interacting with the constituent of interest to produce a detectable or measurable response. The test strip further comprises an infrared dye, applied either to the support strip or incorporated into a test pad, which ensures proper alignment of the test strip in an apparatus having a detection system for the detectable or measurable response. The improved test strip reduces the number of erroneous assays for the constituent of interest.

15 Claims, 1 Drawing Sheet

FIG. 1

TEST STRIP FOR THE ASSAY OF AN ANALYTE IN A LIQUID SAMPLE

FIELD OF THE INVENTION

The present invention relates to a test strip for assaying a liquid test sample for the presence or concentration of a particular constituent, e.g., an analyte. More particularly, the present invention relates to an improved test strip comprising: (a) a support handle having (b) one or more test pads positioned thereon, said test pad comprising (i) a carrier matrix incorporating (ii) a reagent composition capable of interacting with the analyte of interest to produce a detectable or measurable response, and (c) an infrared dye, either applied to the support strip and/or incorporated into a test pad. The improved test strips provide a more reliable and accurate constituent assay because the infrared dye ensures that the test strips are properly aligned in an apparatus that detects and measures the test pad response.

BACKGROUND OF THE INVENTION

An important tool in the analysis of fluids is diagnostic test strips. Diagnostic test strips have a test pad that incorporates a reagent capable of changing color when contacted by a predetermined constituent in a test sample. The intensity and degree of the color change is correlated to the concentration of the predetermined constituent in the test sample. The absence of a color change indicates that the predetermined constituent is not present in the sample, or at least is present below detectable levels.

Diagnostic test strips are available to assay blood, urine, and other body fluids for a predetermined constituent. Diagnostic test strips also are used to determine the presence and/or concentration of constituents in such diverse fluids as water and wine. The test strips utilize different reagents to selectively respond to different predetermined constituents. Accordingly, test strips are available to assay for various constituents, such as those found in urine. The urine assay results allow medical personnel to diagnose various disease states and to institute a proper therapy.

It is important to accurately measure the concentration of an unknown or analyte in a test sample because an inaccurate measurement can lead to an erroneous interpretation of the test result. Investigators, therefore, continually strive both for test strips that eliminate, or at least minimize, the occurrence of false positive and false negative assay results, and for detection apparatus that accurately determine the color of the test strip such that the color change of the strip can be properly correlated to the concentration of the unknown or analyte in the test sample.

In a typical analysis using a test strip, the test strip is dipped in a test sample (such as urine), excess test sample is blotted from the test strip, and the test pad is examined for a color change. The color change of a test strip can be determined by simple observation using the human eye, wherein comparison of the color change to a standardized chart allows correlation of the color change to an unknown or analyte concentration.

Such visual observation is suitable for some assays, but other assays require a more sophisticated detection and measurement method. Therefore, for various assays using a test strip, it is useful to utilize a detection apparatus, like a spectrophotometer, to detect and measure the color change resulting from contacting the test strip with a test sample.

In urinalysis, a conventional spectrophotometer determines the color change resulting from disposing a urine sample on a test pad. The test strip then is placed at a designated location in the spectrophotometer, and a start button is pressed which causes the spectrophotometer to automatically process and inspect the reagent strip. The spectrophotometer illuminates the pad and takes a number of reflectance readings from the pad, each having a magnitude relating to a different wavelength of visible light. The color of test pad then is determined from the relative magnitudes of red, green, and blue reflectance signals.

Conventional spectrophotometers can be used to simultaneously perform a number of different urinalysis tests by utilizing a test strip on which a number of different reagent pads are disposed. Such a reagent strip, like MULTISTIX®, available from Bayer Corporation, Elkhart, Ind., can have ten different reagent pads for assaying ten different analytes. Each reagent pad incorporates a different reagent which results in a color change in response to the presence of a different constituent in urine, such as leukocytes (white blood cells) or red blood cells.

For example, a spectrophotometer has been used to detect the presence of red blood cells in a urine sample. Red blood cells present in the urine react with the reagent incorporated into a test pad, causing the test pad to change color to a degree related to the concentration of red blood cells in the urine sample. In the presence of a relatively large concentration of red blood cells, the test pad changes in color from yellow to dark green.

As stated above, a conventional reflectance spectrophotometer detects the concentration of red blood cells in urine by illuminating the test pad and detecting, via a conventional reflectance detector, the amount of light received from, i.e., reflected from, the test pad. The reflected light is related to the color of the reagent pad. Based upon the magnitude of the reflectance signal generated by the reflectance detector, the spectroscope assigns the urine sample to one of a number of categories, e.g., a first category corresponding to no blood (negative), a second category corresponding to a trace concentration (lysed or intact), a third category corresponding to a small blood concentration, a fourth category corresponding to a medium blood concentration, and a fifth category corresponding to a high blood concentration. From the assay, a diagnosis is made, and a treatment regimen is instituted.

A problem encountered when using a spectrophotometer to measure, or read, the color change of a test pad is an inaccurate assay, or a false negative assay result attributed to an improper alignment of the test strip in the spectrophotometer. Typically, a detection apparatus requires some type of optical positioning or calibration relative to the position of the test strip being read by the detection apparatus. Optical positioning of the test strip presently ig accomplished by: (1) controlling the physical position of the strip either by attaching the strip to a roll, confining the strip in a track, or moving the strip along rails, and/or (2) by checking for predetermined reagents by measurement of a visible color.

A major disadvantage with the above approaches is that they rely on medical laboratory personnel or instrument mechanics to accurately position the test strip with respect to the optics of the detection device. These methods are not fail-safe, and misalignment occurs relatively frequently. Such misalignments result in erroneous analyte assays, but are neither recognized nor recorded as assay errors.

Relying solely on laboratory personnel or instrument mechanics without a fail-safe mechanism for proper alignment of a test strip in a detection apparatus can result in more than 1 in 100 strips being read incorrectly. Checking the pad for a visible color increases reliability, but measuring pad color attributable to a reagent whose color is dependent on the amount of analyte present in a specimen is limited. For example, a 0.200 inch wide test pad has to be mispositioned by more than 0.110 inch before the fail-safe mechanism is activated, and the detection apparatus rejects the test strip, i.e., does not measure the color of the strip until the strip is properly aligned. Furthermore, as illustrated in the following Table 1, false results occur at a mispositioning of as low as 0.055 inch.

The accuracy of the assays can be further improved by attaching the test strips to fixed positions on a test strip carrier prior to reading of the strip by the detection apparatus. However, this method reduces the ability of the apparatus to handle a variety of different types of test strips, and only is economical in apparatus that read high volumes of identical types of test strips.

to be properly aligned. The detection apparatus, therefore, reads the test strip at the predetermined position for a reflectance. The IR dye absorbs energy in the infrared region. Therefore, if the reflectance is too high (i.e., no IR dye is present to absorb energy), the strip is misaligned and the test strip is rejected. After proper alignment, the test strip is read by the detection apparatus, and an accurate analyte assay results.

In one aspect of the invention, the infrared dye is applied to a surface of the support handle of the test strip. In another aspect of the invention, the IR dye is incorporated into a test pad of the strip, either in conjunction with the assay reagent or separately from the assay reagent.

The presence of an IR dye on the test strip ensures a proper alignment of the test strip in the detection apparatus, such that a mispositioning of the strip by about 0.050 inch or more results in the detection apparatus rejecting the test strip. The test strip then is repositioned to allow an accurate

TABLE 1

Effect of Strip Misposition in Spectrophotometer[1]

| Analyte | Expected Result | | | Observed Result | | |
|---|---|---|---|---|---|---|
| Glucose | 100 mg/dL[2] | 100 mg/dL | 100 mg/dL | 100 mg/dL | 0 mg/dL | 0 mg/dL |
| Ketone | Trace | Trace | 0 mg/dL | NM | 0 mg/dL | 0 mg/dL |
|  | 15 mg/dL | 15 mg/dL | 15 mg/dL | 15 mg/dL | 0 mg/dL | 0 mg/dL |
|  | 40 mg/dL | NM | NM | NM | 0 mg/dL |  |
| Protein | Trace | Trace | 0 mg/dL | NM | 0 mg/dL | 0 mg/dL |
|  | 30 mg/dL | NM | NM | NM | NM | 0 mg/dL |
|  | 300 mg/dL | 300 mg/dL | 300 mg/dL | 100 mg/dL | NM | 0 mg/dL |
| Urobilinogen | 1.0 mg/dL | 1.0 mg/dL | 0.2 mg/dL | 0.2 mg/dL | NM | 0.2 mg/dL |
| Bilirubin | Small | Small | 0 mg/dL | 0 mg/dL | NM | 0 mg/dL |
| Strip[3] Misposition (in inches) | 0" (inch) | 0.05" | 0.06" | 0.07" | 0.08" | 0.10" |

[1]Spectrophotometer was a CLINITEK ® 50, available from Bayer Corporation, Elkhart, IN, which relies on the user to align the test sample in a track, and utilizes a pad check for a visual color as a fail-safe. No strips were rejected in this test by the pad position check;
[2]mg/dL is milligrams per decilites;
[3]strips were 0.200 inch wide; and
[4]NM-not measured.

The results summarized in Table 1 demonstrate that a strip can be mispositioned by up to 0.110 inch, and still not be rejected by the position checks utilized in the detection apparatus. At a mispositioning of greater than 0.055 inch, some low-level positive assays were reported as false negative results. By mispositioning by 0.110 inch, almost all assays, even at moderate positive levels, were reported as false negative. The current positioning method uses the inherent color of the test pads as a check, but sensitivity is very low because a large tolerance is required due to differences in reagent reactivity with varying positive analyte levels. The present invention is directed to overcoming the problem of misalignment of a test strip in a detection apparatus, and providing a more accurate test strip assay.

SUMMARY OF THE INVENTION

The present invention is directed to an improved dry phase test strip for analyzing a test sample for a predetermined analyte. More particularly, the present invention is directed to a dry phase test strip that ensures proper alignment of the test strip in a detection apparatus, such as a spectrophotometer.

The improved test strips incorporate an infrared (IR) dye at a predetermined position, or location, on the test strip. The detection apparatus must detect the IR dye for the test strip assay of the test strip. Another aspect of the prevent invention, therefore, is to provide a method of eliminating, or reducing the frequency of, misalignment of test strips in a detection apparatus to such a degree that the test strip provides a fail-safe system for detecting the color change of a test pad on a test strip.

The above and other aspects, advantages, and novel features of the present invention will become apparent from the following detailed description of the preferred embodiments showing the increased assay reliability and accuracy provided by the present test strips because of a proper alignment of the test strip in a detection apparatus.

DETAILED DESCRIPTION OF THE PREFERRED EMBODIMENTS

In accordance with the present invention, a quantitative assay for one or more predetermined constituents in a liquid test samples, like urine, is accomplished utilizing a dry phase test strip comprising: (a) a support handle having positioned thereon (b) one or more test pads comprising an indicator reagent composition incorporated into a suitable carrier matrix. The test strip also comprises an IR dye at a specific, predetermined location on the strip. By employing a test strip comprising an IR dye, the test strip can be monitored for correct positioning in a detection apparatus used to detect and measure the color change of a test pad in response to an analyte.

Proper alignment of a test strip in a detection apparatus results in a more accurate and trustworthy analyte assay. In accordance with an important feature of the present invention, if the test strip is not properly aligned in the detection apparatus, the apparatus rejects the test strip, and will not perform a measurement until the test strip is properly aligned in the apparatus. Accordingly, the occurrence of false negative assay results is substantially reduced, or eliminated, which in turn provides a more trustworthy assay. The accuracy of the assay also is improved because the test pad is properly positioned in the optical pathway of the detection apparatus which results in improved reflectance measurements.

A reliable analyte assay provided by a present test strip can be performed either by a physician to help diagnose disease or condition, or by a physician or an individual at home to help monitor the course of a medical treatment for a disease or condition. An accurate assay for a predetermined analyte can monitor patient compliance, quality of care, and the efficacy of a particular therapy. Therefore, in accordance with the present invention, the concentration of an analyte in a physiological fluid, like urine or blood, can be measured at sufficient intervals, either at home or in a medical office, to accurately and reliably detect a disease or condition or to detect any improvement or deterioration in control of the disease. Similarly, quality control personnel can perform an accurate assay for a constituent in a liquid, like water and wine, using a present test strip.

An IR dye useful in the present invention has a strong absorbance in the infrared region. The identity of the IR dye is not otherwise limited. Preferred IR dyes lack a visible color because such dyes have a low tendency, if any tendency at all, to interfere with measurement of the color change of the strip, and, accordingly, do not adversely affect performance of the test strip. In embodiments wherein the IR dye is incorporated into a test pad, the IR dye cannot adversely affect the reagent incorporated into the test pad or adversely affect an interaction between the analyte of interest and reagent present in the test pad.

Infrared (IR) radiation is that portion of the electromagnetic spectrum between the visible and microwave regions. In that broad region, the portion between about 700 nm and about 2500 nm is the near-infrared (i.e., near-IR or NIR). The portion of the electromagnetic spectrum visible to man is between 400 nm and 700 nm. Many different classes of dyes are known to have absorbances in the IR, and particularly the NIR region. Among the IR dyes are phthalocyanine and naphthalocyanine compounds, metal complex dyes (such as dithiolene metal complex dyes), and the large class of polymethine dyes, including the cyanine dyes. Other classes of NIR dyes include the di- and triphenylmethane dyes, quinone dyes, certain azo dyes, and charge transfer and charge resonance dyes. Additional IR dyes are described and disclosed in J. Fabian, *Chem. Rev.*, 92, pp. 1197–1226 (1992), incorporated herein by reference.

In general, any IR dye, and especially any NIR dye, can be used in the present invention. Choice of a specific dye depends on the optical system used for its detection, compatibility with the method used for its application to the test strip, stability, and cost. An IR dye having a strong absorbance in the range of 825–855 nm is preferred. It is also desirable that the dye lacks a visible color. Generally, a preferred dye has an absorbance in the visible region (i.e., 400–700 nm) less than 20% that of the absorption maximum of the dye in the NIR region. More preferably, this visible absorbance is less than 10%.

The following Table 2 illustrates nonlimiting examples of useful IR dyes. Other useful IR dyes are known to persons skilled in the art. Table 2 also includes IR and visible absorbance data for the listed dyes. The IR dye is present on the test strip in an amount of about 0.05 to about 0.3, and preferably about 0.07 to about 0.2 microgram ($\mu$g) per strip. To achieve the full advantage of the present invention, the IR dye is present on the test strip in an amount of about 0.1 to about 0.2 $\mu$g/strip, either on the handle or incorporated into a test pad.

TABLE 2

| | Dye | IR Absorbance | Maximum Visible Absorbance |
|---|---|---|---|
| 1. | 5, 5'-dichloro-11-diphenylamino-3, 3'-diethyl-10, 12-ethylene-thiatricarbocyanine perchlorate (IR-140)[1] | 1.9 AT .01 mg/mL THF/MeOH 809 nm | 400–570 nm: .05 at 426 nm 570–700 nm: increases to .4 at 700 nm |
| 2. | 3-(5-carboxypentyl)-2-[2-[3[[3-(5-carboxypentyl)-1,3-dihydro-1,1-dimethyl-2H-benz[e]indol-2-ylidene]ethylidene]-2-(2-sulfoethylthio)-1-cyclohexene-1-yl]ethenyl]1,1-dimethyl-1H-benz[e]indolinium, inner salt (DTO-108)[2] | 2.2 at 0.1 mg/dL THF/MeOH 827 nm | Maximums: .1 at 465 nm; .03 at 544, 583 nm; increases from 600 to 700 nm to .2 at 700 nm |
| 3. | 3-(5-carboxypentyl)-2-[2-[3-[[3-(5-carboxypentyl)-1,3-dihydro-1,1-dimethyl-2H-benz[e]indol-2-ylidene]ethylidene]-2-(n-hexylthio)-1-cyclohexen-1-yl]ethenyl]-1,1-dimethyl-1H-benz[e]indolium, inner salt (DTO-141)[2] | 2.2 at 0.1 mg/dL THF/MeOH 827 nm | Maximums: .1 at 465 nm; .03 at 544, 583 nm; increases from 600 to 700 nm to .2 at 700 nm |
| 4. | Copper (II) 5, 9, 14, 18, 23, 27, 32, 36-octabutoxy-2,3-naphthalocyanine | 1.55 at 0.1 mg/mL THF/MeOH 840 nm | Maximum of .15 at 465 nm, increases from 650 to 700 nm (.1 at 700 nm) |

TABLE 2-continued

| Dye | IR Absorbance | Maximum Visible Absorbance |
|---|---|---|
| 5. 5, 9, 14, 18, 23, 27, 32, 36-octabutoxy-2,3-naphthalocyanine (No Metal) | 1.75 at 0.1 mg/mL THF/MeOH 861 nm | Maximum of .15 at 465 nm, increases from 650 nm to 700 nm (.1 at 700 nm) | mg/mL: milligram per milliliter
THF: tetrahydrofuran
MeOH: methanol
nm: nanometers.
[1])Available from Aldrich Chemical Co., Milwaukee, WI;
[2])These dyes were prepared from a reaction between a precursor disclosed in Lee et al. U. S. Pat. No. 5,453,505, and mercaptoethane sulfonic acid sodium salt or hexanethiol according to the general method disclosed in Harada et al. U. S. Pat. No. 5,445,930. The precursor is known by Chemical Abstract Service (CAS) registry number [174829-19-7].

Dyes 1–5 and a precursor to such dyes, i.e., CAS Registry No. [174829-19-7] are illustrated below:

(Precursor)

(Dye 1)

(Dye 2)

(Dye 3)

(Dye 4)
$R^1 = OCH_2CH_2CH_3$ (Dye 5)
$R^1 = OCH_2CH_2CH_3$

Each dye 1 through 5 listed in Table 2 provides useful and strong IR absorbances. As discussed in detail hereafter, dyes 1–5 were applied to the handle of a test strip, or incorporated into a test pad, to provide a test strip of the present invention. The following table illustrates that each dye 1 through 5, when tested in a commonly used, commercial spectrophotometer for measuring the color change on a test strip, significantly reduced reflectance of the strip. The reduction in reflectance can be detected by the optics of the spectrophotometer. If a reflectance reduction is not detected, the test strip is misaligned in the detection apparatus. The test strip then is rejected, i.e., is not assayed.

| Dye | Concentration/Solvent Used at 10 µL/Strip | Absorbance on CLINITEK 50[1] |
|---|---|---|
| 1 | 10 mg/50 mL THF[2] | 48–64% |
| 2 | 5 mg/50 mL Water/Methanol | 44–59% |
| 3 | 5 mg/50 mL Water/Methanol | 44–59% |
| 4 | 10 mg/125 mL THF | 44–50% |
| 5 | 10 mg/125 mL THF | 43–50% |
| Control (No Dye) | NA[3] | 79–82% |

[1]Commercially available apparatus, from Bayer Corp., Elkhart, IN;
[2]THF is tetrahydrofuran; and
[3]NA is not applicable.

A test strip of the present invention can be designed either as a single pad test strip (to assay only for a single unknown or analyte) or as a multiple pad test strip (to assay for several unknowns or analytes simultaneously). For either type of test strip, the test strip includes a support strip, or handle, normally constructed from a hydrophobic plastic, and a reagent test pad, comprising a bibulous or nonbibulous carrier matrix. The handle is formed from hydrophobic materials, such as cellulose acetate, polyethylene terephthalate, polycarbonate, or polystyrene. In general, the carrier matrix is an absorbent material that allows the test sample to move, in response to capillary forces, through the matrix to contact the reagent and produce a detectable and measurable color transition.

The carrier matrix can be any substance capable of incorporating the chemical reagents required to perform the assay of interest, as long as the carrier matrix is substantially inert with respect to the chemical reagents, and is porous and/or absorbent relative to the liquid test sample. The expression "carrier matrix" refers to either bibulous or nonbibulous matrices that are insoluble in water and other physiological fluids and maintain their structural integrity when exposed to water and other physiological fluids. Suitable bibulous matrices includes filter paper, sponge materials, cellulose, wood, woven and nonwoven fabrics, and the like. Nonbibulous matrices include glass fiber, polymeric films, and preformed or microporous membranes. Other suitable carrier matrices include hydrophilic inorganic powders, such as silica gel, alumina, diatomaceous earth, and the like; argillaceous substances; cloth,; hydrophilic natural polymeric materials, particularly cellulosic material, like cellulosic beads, and especially fiber-containing papers such as filter paper or chromatographic paper; synthetic or modified naturally occurring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. Hydrophobic and nonabsorptive substances are not suitable for use as the carrier matrix of the present invention. The carrier matrix can be of different chemical compositions, or a mixture of chemical compositions. The matrix also can vary in regards to smoothness and roughness combined with hardness and softness. However, in every instance, the carrier matrix must include a hydrophilic or absorptive material. The carrier matrix is most advantageously constructed from bibulous filter paper or nonbibulous polymer films.

In accordance with one embodiment of the present invention, the IR dye is applied to a predetermined location on the handle. For example, a stripe of IR dye can be applied to the handle adjacent to the test pad of a single pad test strip. In the case of a multiple pad test strip, the IR dye can be applied to the handle as a stripe in the space between two adjacent test pads.

Figure 1:
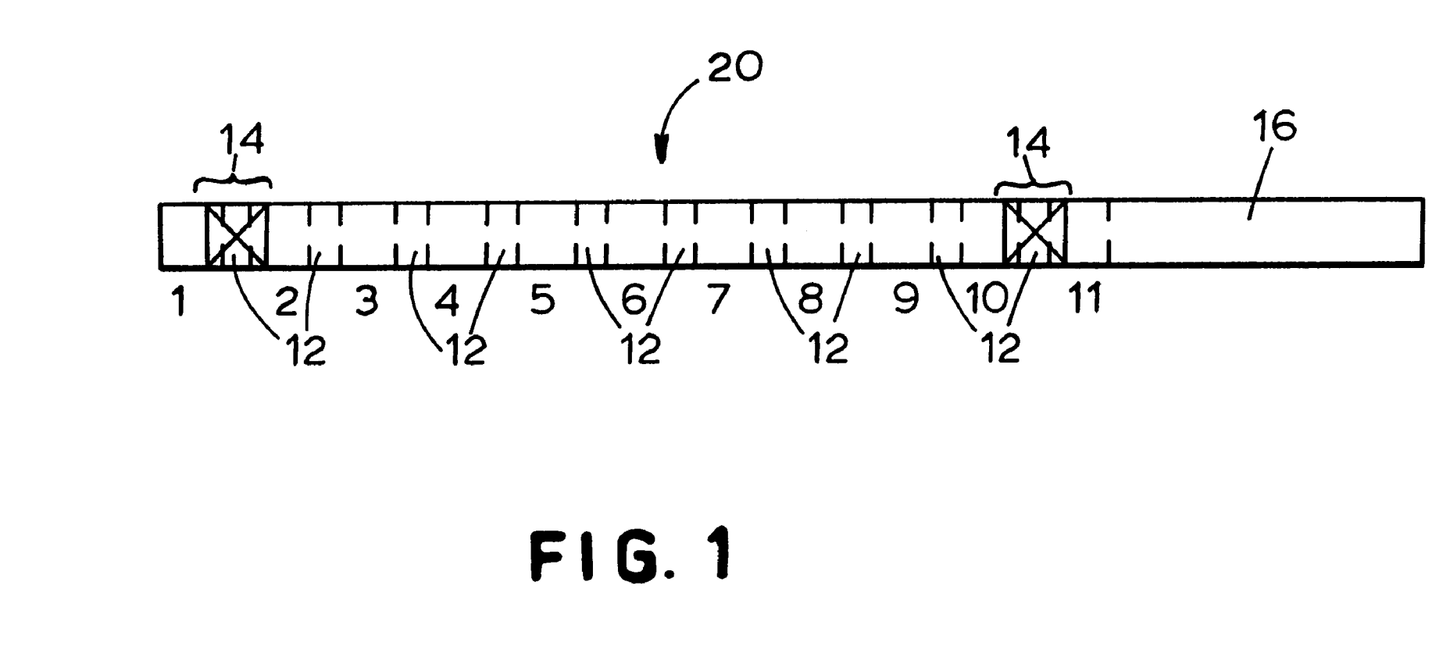
FIG. 1 is a top view of one embodiment of a test strip of the present invention.

This embodiment of the present invention is illustrated in FIG. 1. In particular, FIG. 1 illustrates a multiple reagent test strip 20 containing eleven test pads numbered 1 through 11 on a handle 16. Between each test pad is a space 12 exposing handle 16. Positioned on handle 16 between, and overlapping, test pad 1 and test pad 2, and test pad 10 and test pad 11, is an infrared dye 14.

Alternatively, the IR dye can be incorporated into a test pad. The IR dye can be applied as a component of the reagent composition, or can be applied to the test pad separately from the reagent. In addition, the IR dye can be applied at more than one predetermined position on the test strip, such as both on the handle and in a test pad, or in two test pads, to provide additional checks for proper alignment of the test pad in the detection apparatus.

The resulting dry phase test strip is used in accordance with methods well known in the art. As stated above, the assay for a predetermined analyte is performed by contacting the test sample with a test strip. The test strip can be dipped into the test sample, or the test sample can be applied to the test strip dropwise. The resulting change in color of the test pad demonstrates the presence of analyte and the resulting color transition can be measured spectrophotometrically to provide a quantitative assay for the concentration of analyte in the test sample.

During detection and measurement of the color change in the spectrophotometer, readings are taken at the predetermined locations where the IR dye is present on the test strip. If the test strip is properly aligned, the detection apparatus recognizes the presence of the infrared dye at the predetermined location (i.e., a sufficiently low reflectance reading results because the IR dye absorbs the incident energy), and the apparatus scans or otherwise reads the test strip. If the test strip is not properly aligned, the detection apparatus cannot detect the presence of the infrared dye (i.e., a high reflectance results because the IR dye is not in the path of the incident energy), and the test strip is rejected, i.e., no reading or measurement is made.

In practice, algorithms are applied to these reflectance readings to determine the positioning of the test strip in the spectrophotometer. The reflectance readings also can be used to calibrate pixels. If the test strip is not properly aligned in the spectrophotometer, no assay is performed, and the strip is "rejected." A subsequent proper alignment of the test strip allows the spectrophotometer to analyze the test strip. The IR dye applied to the test strip, therefore, reduces or eliminates false negative and erroneously low assays, and improves the reliability, trustworthiness, and accuracy of the analyte assay.

The following examples illustrate two embodiments of the present invention. Example 1 illustrates coating of an IR dye on a handle of a test strip. Example 2 illustrates incorporation of an IR dye into a test pad of a test strip.

EXAMPLE 1

A test strip containing an IR dye on polystyrene handle was prepared from the following materials:

a. Copper (II) 5,9,14,18,23,27,32,36-octabutoxy-2,3-naphthalocyanine IR dye (available from Aldrich Chemical Co., Milwaukee, Wis.) (copper dye)

b. DTO-108 IR dye c. THF d. Methanol e. Distilled Water f. White hydrophobic polystyrene g. Reels (⅕" width) of a test pad incorporating a reagent that changes color in response to nitrite (nitrite reel)

h. Reels (⅕" width) of a test pad incorporating a reagent that changes color in response to white blood cells (WBC reel)

i. Printing ink (American Inks and Coatings, C11462-M19 Extender)

i. Triethylamine (TEA)

k. White 10 mil thick polystyrene (10 inch square cards).

Test strips having an IR dye applied to the plastic handle were prepared as follows. A solution of the DTO-108 IR dye in methanol/water (10 mg/dL) was prepared. A solution of the copper dye in ink (0.5 mg dye/g ink) also was prepared by dissolving the dye in the ink. In addition, a solution of DTO-108 dye in the printing ink (0.2 mg dye/g ink) was prepared by first dissolving the DTO-108 dye in methanol, then adding triethylamine, followed by air drying. Then, the resulting dye powder was dissolved in ink.

In one embodiment, polystyrene cards were dipped in the DTO-108 dye solution, then air dried. WBC and nitrite reagent reels were laminated onto the coated polystyrene cards. The polystyrene cards were cut on a Ruff Slitter into strips ⅕ inch in width and stored in bottles. In other embodiments, the IR dye ink solutions were coated on the polystyrene cards using a Meyer Rod Apparatus at various thicknesses. WBC and nitrite reagents were laminated onto a portion of the cards. The cards then were slit on Ruff Slitter and bottled.

EXAMPLE 2

The following materials were used to make a nitrite test pad incorporating an IR dye:

a. A test pad incorporating a reagent that changes color in response to nitrite (nitrite test pad)

b. Copper (II) 5,9,14,18,23,27,32,36-octabutoxy-2,3-naphthalocyanine IR dye (available from Aldrich Chemical Co., Milwaukee, Wis.) (copper dye)

c. DTO-108 IR dye d. Tetrahydrofuran (THF)

e. Methanol f. Distilled water.

A test pad containing the DTO-108 IR dye was prepared as follows. A 0.7 mg/dL solution of DTO-108 in 10% distilled water in methanol was prepared. The nitrite test pad then was saturated with the dye solution, and the resulting pad was dried at 50° C. for six minutes. The dried test pad then was laminated on a plastic backing, which then was slit in strips and bottled. Assay results were read on a CLINITEK® 50 scanning-type instrument.

A test pad containing the copper IR dye was prepared as follows. A 1.12 mg/dL solution of the copper dye in THF was prepared. A nitrite test pad then was saturated with the dye solution, and the resulting test pad was dried at 50° C. for six minutes. The dried test pad then was laminated on a plastic backing, which then was slit in strips and bottled. Assay results using the test strips were read on a CLINITEK® 50 instrument.

With respect to applying an IR dye to the handle of the test strip as in Example 1, the translucency of the various reagents relative to their algorithm was considered. Also considered was the variability of test strip manufacturing process. Therefore, in order to provide a coating of the IR dye that completely coats the space (i.e., 0.100 in) between adjacent test pads on a multipad test strip, a 0.125 to 0.200 inch, and preferably a 0.150 to 0.180 inch, coating width of the IR dye is used. This results in up to a 0.100 inch coating under the test pads adjacent to the IR stripe. In a multipad test strip, the space between nitrite test pad and the white blood cell (WBC) test pad was chosen as a preferred position for the IR dye on the handle because, as stated above, an IR reflectance is not used in the algorithm for the nitrite assay, and the WBC test pad uses a kinetic algorithm, go the effect of IR reflectance is minimized.

In Example 2, the IR dye was incorporated into a nitrite test pad. A nitrite test pad is the most preferred pad for incorporation of the IR dye because an IR reflectance reading is not used in the algorithm for measuring the color change resulting from a nitrite concentration of a test sample. Another preferred test pad for incorporation of the IR dye is the occult blood test pad. However, although measurement of the occult blood (OB) assay does not rely upon IR reflectance measurements, the IR absorbance in this assay increases with analyte concentration because the indicator used in the OB assay becomes IR absorbing after oxidation by the analyte. The IR absorbance of the reagent used in the nitrite test does not change with reagent reactions, and, therefore, incorporation of the IR dye into the nitrite pad is most preferred.

All other test pads, except for nitrite and occult blood test pads, use IR reflectance measurements in the algorithm for analyte measurement, and thus the presence of an IR dye in these test pads could effect assay results. However, the IR dye can be included in any test pad because proper adjustments can be made by persons skilled in the art to account for the IR reflectance resulting from ingredients of the reagent composition. Persons skilled in the art are capable of identifying the IR reflectance attributable to the IR dye, and separating this IR reflectance from an IR reflectance contributed by reagent ingredients.

The test strips prepared above in Examples 1 and 2 were read using basic IR reflectance measurements. Several different CLINITEK® 50 instruments in Test Mode 1 were used. The strips were positioned to allow the instrument to read the coated space on the strip as a reagent.

For these test strips, algorithms were determined such that misaligned test strips could be detected, and, therefore, rejected if necessary. The algorithms were determined as follows. A CLINITEK® 50 was programmed with software which reads and outputs IR reflectance every 0.010 inch. The CLINITEK® 50 was used to read test strips having DTO-108 dye incorporated into a nitrite test pad, and test strips having a DTO-108 dye solution coated on polystyrene. Data was evaluated manually to arrive at the following algorithms which detect test pad mispositioning:

a. Dye in nitrite pad:
(1) Nitrite IR reflectance at position 6 steps from theoretical center of pad $\leq 50\%$=Error
(2) Blank space reading between nitrite pads reflectance <25%=error b. Dye coated on polystyrene
(1) Reference blank space—Reference at IR space <20%=error
(2) The following two equations both must be satisfied or there is an error:
a. IR (Control of nitrite)>IR (edge of nitrite)>IR (Center of IR Space)
b. IR (Center of Pad)-IR (Center of IR Space)$\geq 15\%$.

The algorithms involve taking IR reflectance readings at specific positions on the test strip and comparing the reflectance values either to each other or to previously determined fixed values, or both. For the nitrite pad embodiment, one reading is taken, i.e., at IR1, a theoretical position six steps from the center of the nitrite pad in the direction of the white blood cell pad. The algorithm is IR≧>50%.

For the handle coating embodiment, three reflectance readings are taken: (1) at a theoretical center of space between the WBC and nitrite test pads, i.e., IR1, (2) at a theoretical edge of the nitrite test pad, i.e., IR2, (3) theoretical center of the nitrite pad, i.e., IR3. The algorithms are: IR1<IR2<IR3 and IR3−IR1≧15% reflectance. As the strip is mispositioned farther from its proper "full-in" position, both of these relationships eventually are violated and a mispositioning is reported. Examples 1 and 2 show further that any IR dye can be used to achieve proper positioning of the test strip in a detection apparatus.

In summary, test results showed that for a nitrite test pad incorporating an IR dye, mispositioning of between 0.030" and 0.050" was detected on ten strips. No strip was mispositioned by more than 0.050" without detection of the misalignment. For an IR dye positioned on a plastic handle between the nitrite and WBC test pads, mispositioning of between 0.030" and 0.050" was detected on ten strips. No strip was mispositioned by more than 0.050" without detection of the misalignment.

The following Example 3 illustrates the effect of positioning a colored, visible dye on a test strip, and using that visible dye in an attempt to ensure proper positioning of a test strip in a detection apparatus.

EXAMPLE 3

Materials a. Colored adhesive tapes - red, blue, green and black
b. White hydrophobic polystyrene
c. MULTISTIX® 10 SG reagent pad reels:
   white blood cells   occult blood
   nitrite             specific gravity
   urobiliogen         glucose
   protein             ketones
   pH                  bilirubin
d. Black bottles, caps, molecular sieve desiccant
e. CLINITEK® 50 spectrophotometer
f. MAS 1
g. White blood cell reagent (10 cells/$\mu$L)
h. Nitrite solution(1 g/dL)

Method a. Five sets of MULTISTIX® 10 SG test strips were assembled, slit, and bottled, as follows:
   (1) Control—no colored tape (To add height to Control, a blank plastic handle under control strips, having the same height as the color tape, also was present.)
   (2) Red—red tape positioned between test pads and polystyrene
   (3) Green—green tape positioned between test pads and polystyrene
   (4) Black—black tape positioned between test pads and polystyrene
   (5) Blue—blue tape positioned between test pads and polystyrene
b. All test strips were read on CLINITEK® 50 apparatus in Test Mode c. Solutions
   (1) Dilute white blood cell reagent (10 cells/$\mu$L) with MAS 1 at 1:1 to provide 5 cells/$\mu$L, 1 drop of nitrite solution was added to make the solution barely positive with respect to nitrite concentration
   (2) MAS1 was used as a negative test for WBC and nitrite To demonstrate the effect of a visible dye, the above four different color tapes, i.e., red, green, blue, and black, were laminated to different plastic handles, and then all ten reagent pads present on a MULTISTIX® 10 SG test strip were laminated onto the handles. The results, for both negative and positive test solutions for these colored tape strips, were compared to control strips mounted on an extra thick handle to equal the tape strip thickness. With all reagents used on a MULTISTIX® test strip, some or all of the colored tapes caused either false positive or false negative test assays. These results (Table 3) show that a visibly colorless dye, i.e., an IR dye, must be used as the marker to ensure proper alignment of a test step in a spectrophotometer.

TABLE 3

| Solution | Reagent | Control | Red | Blue | Green | Black |
| --- | --- | --- | --- | --- | --- | --- |
| MAS 1 (as a | Bilirubin | N | Sm | L | L | N |
| negative | Protein | N | 30 | 100 | 100 | N |
| control | Blood | N | N | Tr | Tr | Tr |
| solution) | Specific Gravity | 1.010 | 1.010 | 1.010 | 1.010 | 1.020 |
| MAS 1 (containing white blood cells and nitrite) | Nitrite | Pos | | N | N | |
| | Leukocyte | Tr | | N | N | |

N = negative assay
Pos = positive assay
Tr = trace assay
Sm = small concentration
L = large concentration The data in Table 3 demonstrates that an IR dye, which lacks a visible color, is the only type of dye that can serve as a marker to ensure correct alignment of a test strip in the detection apparatus. In particular, a visible dye absorbs light at the red, green, and/or blue wavelength bands used by the spectrophotometer. Such an absorption affects performance of the test pad reagents because test pads all are translucent to a degree when wet (i.e., are "available" to be read by detection apparatus), and all use one or more of the visible wavelengths in their respective algorithm.

The CLINITEK® 50 detection apparatus used in the above examples is a scanning type of instrument. The following Example 4 illustrates that the present test strips also are useful in alignment and optical calibration of camera-type instruments. A camera-type instrument uses a CCD camera to create a multipixel image at one time (see following Table 5). In this case, a method of aligning the multipixel image is required, i.e., determining which positions on the strip correspond to which pixel.

Accordingly, when using a camera-type instrument (e.g., a Bobcat SWM #6), two IR dye stripes on the handle, or one IR dye stripe on the handle and an IR dye incorporated into one pad, separated by known distances, can be used to "align" the pixel image each time a strip is read. The Bobcat instrument is an analyzer used for measuring the reflectance of diagnostic test strips utilizing a uniform illumination of the strip by multiple LEDs and linear array detection.

Similar to a scanning-type of instrument, color dye stripes cannot be used in a camera-type apparatus. Colored stripes cannot be used because the color at least slightly affects performance of all reagents due to manufacturing tolerances and translucence of wet test pads. Other methods of pixel calibration, such as factory calibration of pixel alignment, rely upon the user to place the test strip accurately in the track. This prior method does not address the problem of the user mispositioning test strips in the holder.

The IR dyes are positioned on the test strip at a predetermined separation, and using the IR dye containing stripes or test pads for calibration corrects mispositioning of the strip in the apparatus holder. Data presented in Table 5 demonstrates this embodiment of the invention.

EXAMPLE 4

A. Materials
1. DTO-108 dye and triethylamine were added to methanol. The methanol and excess triethylamine were allowed to evaporate, leaving an amorphous powder of the IR dye
2. Clear 3 mil thick mylar
3. Translucent 3.5 mil thick mylar
4. Reagent compositions (⅕ inch reels)
   a. white blood cell
   b. nitrite
   c. glucose
5. Double stick adhesive
6. Black bottles and caps
7. Molecular sieve desiccant
8. Ink base
9. White 10 mil thick polystyrene (10 inch square cards)
10. Bobcat SWM #6 (CCD-type detection apparatus)

B. Method

The amorphous dye powder was dissolved in the ink base (0.2 mg dye/g ink). The resulting solution then was coated on mylar at a thickness of 1.62 mil, and an adhesive was applied to the coated mylar. The resulting coated mylar was slit into ⅔ inch wide ribbons, and reels of coated mylar/adhesive (⅔ inch) were applied to the polystyrene cards at (a) at position 11, and (b) near the tip. Reagents then were applied to the cards over the mylar as follows:
   a. white blood cell—position 1 (tip)
   b. nitrite—position 2
   c. glucose—position 10.

The cards then were slit into ⅕ inch strips, bottled in 48 mm black bottles, and capped and labeled (Clear1, Clear2, Mylar1, and Mylar2). Five strips from each bottle were dipped in MAS1 solution and bottled. The strips then were read on a Bobcat SWM #6 fitted and 845 nm LED, and data was collected and analyzed.

C. Algorithms Used (256 pixel CCD in Bobcat)
1. Pixel 1$a$=midpoint between white blood cell and nitrite
2. Pixel 1$b$=minimum between white blood cell and nitrite
3. Pixel 2$a$=first reading more than 10% R lower than glucose (R>80%).
4. Pixel 2$b$=first reading beyond glucose which is <75% R
5. Pixel 2$c$=first reading beyond glucose which is <50% R.

Calculations were as follows:
1. 2$a$-1$a$
2. 2$a$-1$b$
3. 2$b$-1$a$
4. 2$b$-1$b$
5. 2$c$-1$a$
6. 2$c$-1$b$

TABLE 5

Data Using Bobcat for Test Strips Raving IR Dye Stripes

| | | Pixel Number | | | | | | | | | | |
|---|---|---|---|---|---|---|---|---|---|---|---|---|
| Type | Strip | 1a | 1b | 2a | 2b | 2c | 2a–1a | 2a–1b | 2b–1a | 2b–1b | 2c–1a | 2c–1b |
| Clear1 | 1 | 30.5 | 32 | 223 | 224 | 225 | 192.5 | 191 | 193.5 | 192 | 194.5 | 193 |
|  | 2 | 30.5 | 31 | 223 | 224 | 225 | 192.5 | 192 | 193.5 | 193 | 194.5 | 194 |
|  | 3 | 30.5 | 31 | 223 | 224 | 225 | 192.5 | 192 | 193.5 | 193 | 194.5 | 194 |
|  | 4 | 34.5 | 36 | 227 | 228 | 229 | 192.5 | 191 | 193.5 | 192 | 194.5 | 193 |
|  | 5 | 36.0 | 37 | 228 | 230 | 230 | 192.0 | 191 | 194.0 | 193 | 194.0 | 193 |
| Clear2 | 1 | 30.0 | 31 | 223 | 224 | 225 | 193.0 | 192 | 194.0 | 193 | 194.0 | 194 |
|  | 2 | 30.5 | 32 | 223 | 224 | 225 | 192.5 | 191 | 193.5 | 192 | 193.5 | 193 |
|  | 3 | 30.5 | 32 | 223 | 225 | 236 | 192.5 | 191 | 194.5 | 193 | 194.5 | 194 |
|  | 4 | 30.5 | 32 | 223 | 225 | 225 | 192.5 | 191 | 194.5 | 193 | 194.5 | 193 |
|  | 5 | 34.5 | 36 | 227 | 228 | 229 | 192.5 | 191 | 193.5 | 192 | 194.5 | 193 |
| Mylar1 | 1 | 30.0 | 31 | 224 | 225 | 226 | 194.0 | 193 | 195.0 | 194 | 194.0 | 195 |
|  | 2 | 30.5 | 31 | 224 | 225 | 226 | 193.5 | 193 | 194.5 | 194 | 194.0 | 195 |
|  | 3 | 30.0 | 31 | 224 | 225 | 226 | 193.5 | 193 | 195.0 | 194 | 194.0 | 195 |
|  | 4 | 30.0 | 31 | 223 | 224 | 225 | 193.0 | 192 | 194.0 | 193 | 193.0 | 194 |
|  | 5 | 34.0 | 35 | 227 | 228 | 229 | 193.0 | 192 | 194.5 | 193 | 193.0 | 194 |
| Mylar2 | 1 | 30.0 | 31 | 223 | 224 | 225 | 193.0 | 192 | 194.0 | 193 | 195.0 | 194 |
|  | 2 | 29.5 | 31 | 223 | 224 | 225 | 193.5 | 192 | 194.5 | 193 | 195.5 | 194 |
|  | 3 | 30.5 | 31 | 223 | 224 | 225 | 193.5 | 192 | 193.5 | 193 | 194.5 | 194 |
|  | 4 | 30.5 | 31 | 223 | 224 | 225 | 193.5 | 192 | 193.5 | 193 | 194.5 | 194 |
|  | 5 | 34.5 | 36 | 228 | 229 | 230 | 193.5 | 192 | 194.5 | 193 | 195.5 | 194 |

The data in Table 5 shows that any of the combinations of algorithms can be used, because all measurements are essentially the same. The gaps remain the same for deliberately misplaced strips (strips numbered 5), and all predict a tip of strip within 1 pixel to 18 pixels from 1$a$.

EXAMPLE 5

A. Materials
1. Hydrophobic Plastic Coated with IR Dye DTO-141
   a. Coating solution (by weight) 0.05% DTO-141 dye 0.3% UVITEX® (Ciba Specialty Chemicals Holding, Inc., Basel, Switzerland) dissolved in SUN- BOND Blend Varnish 61-V-38 printing ink (Sun Chemical Corp., Charlotte, N.C.)
    b. Coated on production Flexo Press at strip positions 1.5 and 10.5 at width of 0.200" for each stripe
  2. Reagent Compositions (⅕ inch reels)
    a. white blood cell (WBC)
    b. nitrite
  3. Double stick adhesive
  4. Black bottle and caps
  5. Molecular sieve desiccant
  6. CLINITEK 50 #218
  7. Multiple Analyte Solution #1
B. Method The amorphous dye powder and the UVITEX® powder were dissolved in the ink base at concentrations of 0.5% and 0.3%, by weight, respectively. The UVITEX® was added to make the coating visible under UV light used to detect "skips" on the press. The solution was applied to 10 mil polystyrene at positions 1.5 and 10.5 on each of seven 4.25" wide portions of the web. This web was slit into 4.25"reels used for strip assembly of strips. Cards of 10 inches each were cut from one of the 4.25" reels of plastic.

The white blood cell reagent was applied to position 1 and the nitrite reagent was applied to position 2 of each card. These cards were then slit into ⅕" strips and bottled in 48 mm black bottles and a desiccant was added and the bottles were capped. Ten strips then were dipped in Multiple Analyte Test Solution and read on the CLINITEK® 50 equipped with special software to detect and output the infrared readings from the strip every 0.010".

C. Algorithms Used

Three reflectance readings are used: (1) IR1 at a theoretical center of space between the WBC and nitrite test pads, (2) IR2 at a theoretical edge of the nitrite test pad, and (3) IR3 at the theoretical center of the nitrite test pad. The algorithms are: IR1<IR2<IR3 and IR3–IR1>15%.

D. Results

All ten test strips violated one or more of the above-listed algorithms at a mispositioning of 0.050" or less. Therefore, any misalignment of 0.050" or more was detected.

It has been demonstrated that providing an IR dye on a test strip, at one or more predetermined, known locations, substantially reduces or eliminates analyte assay errors attributable to mispositioning of a test strip in a detection apparatus. As illustrated above, the IR dye can be applied to the handle of the test strip, incorporated into a test pad of the test strip, or both. The present test strips are useful in both a scanning-type detection apparatus and a camera-type detection apparatus. Therefore, in accordance with an important feature of the present invention, more trustworthy and reliable assays for an unknown or for an analyte content in a test sample, like urine, can be performed by utilizing a test strip of the present invention.

Obviously, many modification and variations of the invention as hereinbefore set forth can be made without departing from the spirit and scope thereof and therefore only such limitations should be imposed as are indicated by the appended claims.

What is claimed is:

1. A test strip for determining the presence or concentration of one or more predetermined analytes in a liquid test sample comprising:
   (a) a support handle;
   (b) one or more test pads positioned on the support handle, each test pad comprising (i) a carrier matrix incorporating (ii) a reagent composition capable of interacting with a predetermined analyte to provide a detectable response; and
   (c) an infrared dye positioned at a predetermined location on the test strip.

2. The test strip of claim 1 wherein about 0.05 to about 0.3 micrograms of the infrared dye are positioned on the test strip.

3. The test strip of claim 1 wherein the infrared dye is positioned on the support handle of the test strip.

4. The test strip of claim 1 wherein the infrared dye is incorporated into one or more test pad.

5. The test strip of claim 1 wherein the infrared dye is incorporated into one or more test pad and positioned on the support handle of the test strip.

6. The test strip of claim 1 wherein the infrared dye absorbs infrared radiation at least at one infrared wavelength.

7. The test strip of claim 6 wherein the infrared dye lacks a visible color.

8. The test strip of claim 1 wherein the infrared dye is selected from the group consisting of 5,5'-dichloro-11-diphenylamino-3,3"-diethyl-10,12-ethylenethiatricarbocyanine perchlorate, 3-(5-carboxypentyl)-2-[2-[3[[3-(5-carboxypentyl)-1,3-dihydro-1,1-dimethyl-2H-benz[e]indol-2-ylidene]-ethylidene]-2-(2-sulfoethylthio)-1-cyclohexene-1-yl]ethenyl]1,1-dimethyl-1H-benz[e] indolinium, 3-(5-carboxypentyl)-2-[2-[3-[[3-(5-carboxypentyl)-1,3-dihydro-1,1-dimethyl-2H-benz[e]indol-2-ylidene]-ethylidene]-2-(n-hexylthio)-1-cyclohexen-1-yl]-ethenyl]-1,1-dimethyl-1H-benz[e]indolium, copper (II) 5,9,14,18,23,27,32,36-octabutoxy-2,3-naphthalocyanine, 5,9,14,18,23,27,32,36-octabutoxy-2,3-naphthalocyanine, and mixtures thereof.

9. The test strip of claim 1 wherein the infrared dye is incorporated into a test pad capable of assaying for nitrite or for occult blood.

10. The test strip of claim 1 wherein the infrared dye is applied to the support handle and is positioned adjacent to a test pad capable of assaying for nitrite.

11. A method of monitoring alignment of a test strip in an optical pathway of a detection apparatus comprising:
   (a) providing a test strip, said test strip comprising
      (i) a support handle;
      (ii) one or more test pads positioned on the support handle, each test pad comprising (i) a carrier matrix incorporating (ii) a reagent composition capable of interacting with a predetermined analyte to provide a detectable response; and
      (iii) an infrared dye positioned at a predetermined location on the test strip;
   (b) inserting the test strip in the detection apparatus;
   (c) illuminating the predetermined location of the infrared dye on the test strip with infrared radiation;
   (d) measuring a reflectance of infrared radiation from the predetermined location on the test strip; and
   (e) correlating the reflectance measurement to the alignment of the test strip in the detection apparatus.

12. The method of claim 11 wherein the detection apparatus is a scanning-type apparatus.

13. The method of claim 11 wherein the detection apparatus is a camera-type apparatus.

14. The method of claim 11 wherein the test strip is rejected by the detection apparatus when misaligned by about 0.05 inch or greater.

15. The method of claim 11 wherein misalignment of the test strip in the detection apparatus by an amount of 0.030 inch or greater is detected.

* * * * *